United States Patent [19]

Krug

[11] Patent Number: 4,671,786
[45] Date of Patent: * Jun. 9, 1987

[54] OVERPRESSURE SAFETY VALVE

[75] Inventor: John A. Krug, Orange, Calif.

[73] Assignee: C. R. Bard, Inc., Murray Hill, N.J.

[*] Notice: The portion of the term of this patent subsequent to Mar. 5, 2002 has been disclaimed.

[21] Appl. No.: 690,552

[22] Filed: Jan. 9, 1985

Related U.S. Application Data

[63] Continuation of Ser. No. 421,027, Sep. 22, 1982, Pat. No. 4,502,502.

[51] Int. Cl.$^4$ ............................................. A61M 16/00
[52] U.S. Cl. ........................................ 604/4; 604/118; 604/247; 604/151; 604/319
[58] Field of Search ............... 604/4, 118, 119, 121, 604/902, 247, 129, 153, 151, 317, 319, 320, 321, 323, 318, 322, 323, 324, 325, 326; 128/DIG. 3; 422/44, 45

[56] References Cited

U.S. PATENT DOCUMENTS

| | | | |
|---|---|---|---|
| 2,652,831 | 9/1953 | Cheslen | 128/DIG. 3 |
| 3,556,122 | 1/1971 | Laerdal | 137/102 |
| 3,626,978 | 12/1971 | Hoekstra | 137/525.3 |
| 3,633,613 | 1/1972 | Julow | 137/512.3 |
| 3,661,174 | 5/1972 | Cripe | 137/512.3 |
| 3,818,929 | 6/1974 | Braukmann | 137/218 |
| 3,905,382 | 9/1975 | Waterson | 137/102 |
| 4,084,606 | 4/1978 | Mittleman | 137/102 |
| 4,540,413 | 9/1985 | Russo | 604/320 |
| 4,544,370 | 10/1985 | Elliott et al. | 604/319 |

FOREIGN PATENT DOCUMENTS

| 1148709 | 5/1963 | Fed. Rep. of Germany | 604/118 |
|---|---|---|---|
| 2082071 | 3/1982 | United Kingdom | 604/319 |

OTHER PUBLICATIONS

Delta Medical Industries, "Do You Vent the Left Heart?"-VRV-200B brochure-1579 Sunland Lane, Costa Mesa, Calif. 92626.

Primary Examiner—Henry J. Recla
Attorney, Agent, or Firm—Spensley Horn Jubas & Lubitz

[57] ABSTRACT

An overpressure safety valve assembly for use during heart surgery is disclosed. The assembly comprises an elongated tubular body portion having an inlet end, and an outlet end and an unidirectional valve disposed therebetween. A relief valve portion is joined to and in flow communication with the tubular portion. The relief valve portion includes a first relief valve configured to open if the pressure within the overpressure safety valve diminishes below a predetermined level, and a second relief valve configured to open if the pressure adjacent the outlet end exceeds a predetermined level.

4 Claims, 3 Drawing Figures

U.S. Patent  Jun. 9, 1987  4,671,786
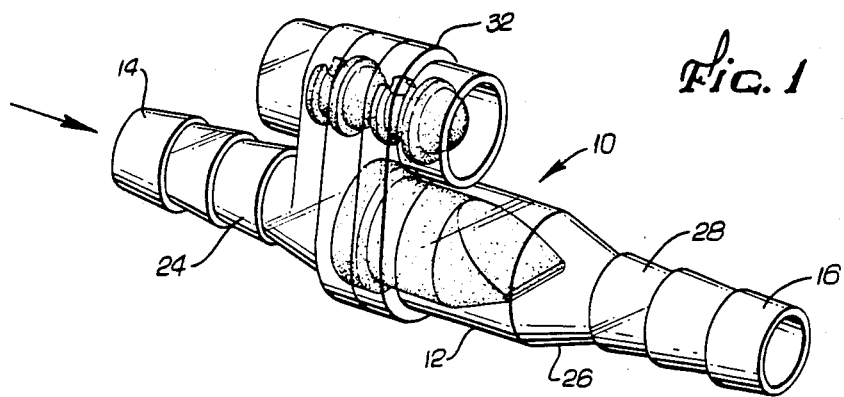
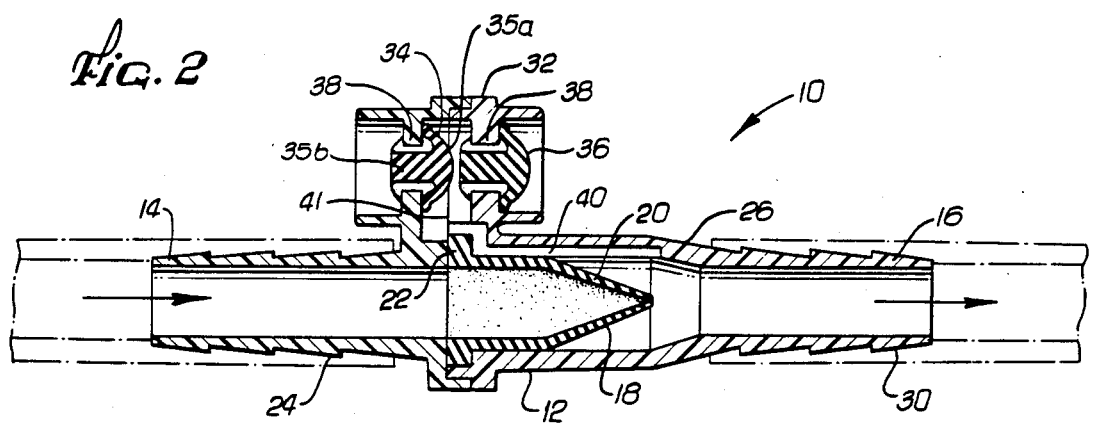
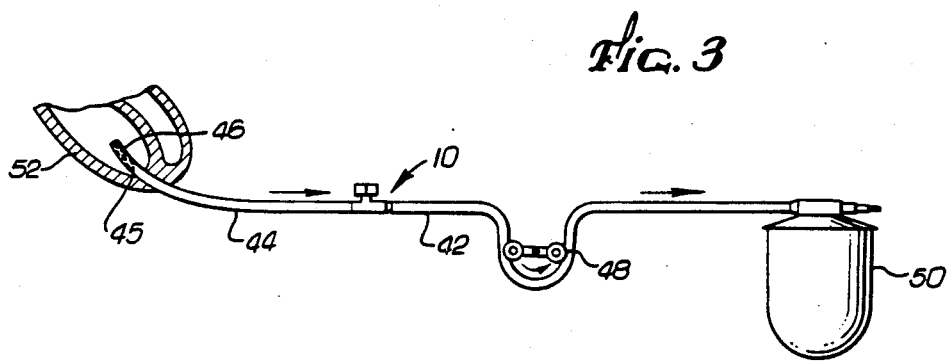

OVERPRESSURE SAFETY VALVE

This is a continuation of application Ser. No. 421,027, filed Sept. 22, 1982, now U.S. Pat. No. 4,502,502.

The term of this patent subsequent to Mar. 5, 2002 has been disclaimed by the assignee.

BACKGROUND OF THE INVENTION

1. Field of the Invention

This invention relates to the field of vent valves, and more particularly, to a vent valve assembly used in heart surgery.

2. Prior Art

During heart surgery, a drainage cannula is often inserted into the heart, and more specifically, into the left ventricle. This cannular is used to drain the blood either by gravity flow or in combination with a pump. The blood is directed through one or more conduits to a cardiotomy reservoir, and then to an oxygenator which oxygenates the blood. Blood flow is then directed back to the patient. It has been found in connection with such a system, that certain advantages can be gained by decompressing the left ventricle during the cardiopulmonary bypass procedure. One of the problems associated with pump drainage is excessive suction. While the amount of suction can be increased, too much suction can cause the conduits to collapse should the drainage cannula become occluded. Even though this problem has been recognized for some time, the solution has proved elusive.

The prior art is well aware of many valve configurations which have been used in a wide variety of medical products as well as in connection with automotive products, and the like. Examples of such valves are disclosed in U.S. Pat. Nos. 3,556,122; 3,572,375; 2,626,978; 3,633,613; 3,661,174; 3,818,929; 3,905,382; 3,941,149; and 4,084,606. Notwithstanding the existance of these different valve configurations, there is no prior art device which has all of the features associated with the overpressure safety valve of the present invention.

SUMMARY OF THE INVENTION

The overpressure safety valve assembly of the present invention comprises an elongated tubular body portion having an inlet end and an outlet end. The inlet end of the valve is connected to a conduit which, in turn, is connected to a cannula inserted into the left ventricle of the heart. The outlet end of the valve is connected to a conduit which, in turn, is connected to a cardiotomy reservoir. A pump, such as is well known in the art, draws blood from the left ventricle, through the various conduits and the subject cannula vent valve, and into the cardiotomy reservoir. In order to insure blood flow in one direction, a unidirectional flow regulator is disposed along the length of the tubular body portion.

A relief valve portion is jointed to and in flow communication with the tubular body portion. the relief valve portion includes a first relief valve configured to open if the pressure adjacent the outlet end diminishes below a predetermined level, and a second relief valve configured to open if the pressure adjacent the outlet end exceeds a predetermined level. In this manner, unrestricted blood flow from the left ventricle of the heart to the cardiotomy reservoir can be achieved, but backflow into the heart through the conduit is precluded. In addition, the first relief valve limits the vacuum in the line to a predetermined level thereby preventing damage to tissues, especially heart tissues, if the line between the heart and the vent valve assembly becomes occluded. The second relief valve acts as a positive pressure relief valve and relieves any pressure buildup in the line between the pump and the vent valve assembly.

The novel features which are believed to be characteristic of the invention, both as to its organization and method of operation, together with further advantages and objectives thereof, will be better understood from the following description considered in connection with the accompanying drawings in which a presently preferred embodiment of the invention is illustrated by way of example. It is to be expressly understood, however, that the drawings are for the purpose of illustration and description only, and are not intended as a definition of the limits of the invention.

DESCRIPTION OF THE DRAWINGS

FIG. 1 is a perspective view of the overpressure safety valve assembly of the present invention;

FIG. 2 is a cutaway view of the overpressure safety valve assembly of the present invention shown in FIG. 1; and FIG. 3 is a circuit diagram showing the use of the overpressure safety valve assembly of the present invention.

DETAILED DESCRIPTION OF THE INVENTION

Referring first to FIGS. 1 and 2, there is shown, as a presently preferred embodiment, an overpressure safety valve assembly 10 which is comprised of an elongated tubular body portion 12 having an inlet end 14 and an outlet end 16. A unidirectional flow regulator or valve 18 is axially disposed in the body 12 along the length thereof. Such unidirectional valve 18 is well known and recognized in the art sometimes being referred to as a "duckbill" valve. Such a valve 18 includes flap members 20 and an integral base 22 defining a generally cylindrical base opening. Valve body portion 12 is made of a first tubular section 24 and a second tubular section 26 joined together so as to sandwich the base 22 of the valve 18 thereinbetween. Each end 14, 16 of the body 12 has a series of ribbed or barbed members 28 which enable the assembly 10 to be easily joined to flexible conduits as hereinbelow described in greater detail. While each of the sections 24, 26 have preselected diameters, in the preferred embodiment, a reduced diameter portion 30 forms outlet end 16.

Joined to and in flow communication with the tubular body portion 12 is a tubular relief valve portion 32. Relief valve portion 32 includes two inline poppet relief valves 34, 36. Such relief valves 34, 36 are also well known in the art, and sometimes referred to as "umbrella" valves, and include an outwardly extending head 35a and an elongated body 35b. Valves 34, 36 are held in axial alignment along the length of the relief valve portion 32 by mounting flanges 38 which form associated valve seats for each of the valves 34, 36, and a small chamber 41 therebetween. The relief valve portion 32, and more specifically chamber 41, is in flow communication with the tubular body portion 12 by means of a generally trough-like flow channel 40. However, a variety of configurations can be used in order to direct fluid flow from member 12 to member 32.

Referring now to FIG. 3, a circuit diagram is illustrated which shows how the overpressure safety valve assembly 10 of the present invention is utilized. Preferably, a first conduit 42 is joined to the outlet end 16 of the assembly 10, while a second conduit 44 is joined to the inlet end 14. Conduit 44, in turn, is connected to a cannula 45 which, typically, has a series of openings 46 adjacent its distal end. Openings 46 permit the left ventricle of the heart 52 to be drained such as is typically done during a cardiopulmonary bypass operation. In order to insure quick drainage of the left ventricle of the heart 52, a pump 48 is disposed on the outlet side of the valve assembly 10. Such a pump 48 is well known in the art and will not be described in detail herein. Pump 48 usually includes a roller member which rolls along conduit 42 thereby creating a vacuum in conduit 44 and cannula 45. Thus, the blood from the left ventricle of the heart 52 is drawn into the cannula 45 and conduit 44, and through the vent valve assembly 10. Once past the pump 48, the blood is pushed through the remainder of conduit 42 into cardiotomy reservoir 50.

In the operation of the subject overpressure safety valve assembly 10, blood would flow into the inlet end 14 of the valve body portion 12. Sufficient pressure would cause the flap members 20 to open enabling blood to flow through the valve body portion 12 and out the outlet end 16. If for some reason the pump was inadvertently operated such that a "backflow" was created, back pressure would cause the flap members 20 to close thereby preventing flow back into the heart 52. In this manner, the unidirectional valve 18 allows blood flow from the left ventricle of the heart 44 to the cardiotomy reservoir 50, but closes automatically to prevent flow back into the heart.

The first umbrella relief valve 38 operates as a negative pressure relief valve in that it limits the vacuum in the line to approximately 190 mm Hg. That is, should the pressure within the overpressure safety valve decrease to this pressure, umbrella valve 34 would open thus permitting air to be drawn into the body portion 12. In this manner, a potentially dangerous sucking action on the upstream side of the assembly 10 (i.e., in the cannula 45 and heart 44) would be substantially diminished.

The second umbrella relief valve 36 operates as a positive pressure relief valve in that it relieves any pressure buildup in conduit 42 between the pump 48 and the valve assembly 10. More specifically, should the pressure increase adjacent the outlet end 16 (for example should the pump action be inadvertently reversed) such increase pressure will cause umbrella valve 36 to open thus releasing the pressure buildup.

While the preferred embodiment of the present invention has been described by reference to FIGS. 1-3, it will be apparent to those skilled in the art that various other applications of the valves are possible. For example, other types of unidirectional flow regulators are within the scope of the present invention. In the preferred embodiment, the flow axis of members 12 and 32 are substantially parallel; other flow axes are also within the scope of this invention. Further, the preferred embodiment of the present invention contemplates the use of polycarbonate plastics for the elements 12 and 32. Other similar biocompatible materials are also within the scope of the present invention. This invention, therefore, is not intended to be limited to the particular embodiments herein disclosed.

What is claimed is:

1. In a blood flow system having a blood reservoir and a conduit connected thereto for directing blood into said reservoir, the improvement comprising an overpressure safety valve assembly disposed along the length of said conduit and comprising:

an elongated tubular body portion having an inlet portion having a first end including means adapted to be connected to a conduit and an opposite second end, and an outlet portion having a first end including means adapted to be connected to a conduit and an opposite second end, said second ends of said tubular body portion being complimentally configured to each other such that, when joined together, form a flow path through said tubular body, and a unidirectional flow regulator valve having mounting means adapted to be sandwiched between the second ends of said inlet and outlet portions, said second ends of said inlet and outlet portions of said tubular body portions including means configured to receive said mounting means disposed therebetween, said unidirectional flow valve configured for permitting flow through said tubular body portion only from said inlet portion end to said outlet portion end; and a separate tubular relief valve portion joined to said tubular body portion in side by side relation thereto and in flow communication with said outlet portion end of said tubular body portion, said tubular relief valve portion having an inlet portion including first and second ends and an outlet portion having first and second ends, said inlet portion of said tubular relief valve portion being positioned adjacent said inlet portion of said tubular body portion with the second ends of each portion lying substantially in a common plane, said outlet portion of said tubular relief valve portion being positioned adjacent said outlet portion of said tubular body portion with the second ends of each portion lying substantially in a common plane, said second ends of said tubular relief valve portion being complimentally configured to each other, said inlet and outlet portions of said tubular body portion and tubular relief valve portion being connected together with said unidirectional flow valve such that said second ends of each respective portion are joined together with said flow valve in said flow path and wherein said first and second portions of said tubular relief valve portion forms a chamber, a first relief valve mounted in said inlet portion of said tubular relief valve portion upstream of said chamber and configured to open if the pressure within said overpressure safety valve assembly adjacent said outlet portion end falls below a predetermined level, and a second relief valve mounted in said outlet portion of said tubular relief valve portion downstream of said chamber and configured to open if the pressure adjacent said outlet portion end of said overpressure safety valve assembly exceeds a predetermined level, and further wherein said tubular body portion and said tubular relief valve portion defines a flow channel for fluid flow from said outlet portion of said tubular body portion to said chamber.

2. The system according to claim 1 wherein said first and second relief valves are poppet valves.

3. The system according to claim 2 wherein said poppet valves are in an in-line configuration.

4. A method of using an overpressure safety valve assembly for a blood flow system comprising:

flowing blood along a conduit and into a blood reservoir, said conduit housing the overpressure safety valve assembly, wherein the overpressure safety valve assembly includes an elongated tubular body portion with an inlet portion having a first end including means adapted to be connected in flow communication with the conduit and an opposite second end, and an outlet portion having a first end including means adapted to be connected to a conduit and an opposite second end, said second ends of said tubular body portion being complimentally configured to each other such that when joined together, form a flow path through said tubular body, and a unidirectional flow regulator valve having mounting means adapted to be sandwiched between the second ends of said inlet and outlet portions, said second ends of said inlet and outlet portions of said tubular body portions including means configured to receive said mounting means disposed therebetween, and said unidirectional flow valve configured for permitting blood flow through said tubular body portion only from the inlet portion end to the outlet portion end; and a separate tubular relief valve portion joined to said tubular body portion in side by side relation thereto and in flow communication with said outlet portion and of said tubular body portion, said tubular relief valve portion having an inlet portion including first and second ends and an outlet portion having first and second ends, said inlet portion of said tubular relief valve portion being positioned adjacent said inlet portion of said tubular body portion with the second ends of each portion lying substantially in a common plane, said outlet portion of said tubular relief valve portion being positioned adjacent said outlet portion of said tubular body portion with the second ends of each portion lying substantially in a common plane, said second ends of said tubular relief valve portion being complimentally configured to each other, said inlet and outlet portions of said tubular body portion and tubular relief valve portion being connected together with said unidirectional flow valve such that said second ends of each respective portion are joined together with said flow valve in said flow path and wherein said first and second portions of said tubular relief valve portion forms a chamber, a first relief valve mounted in said inlet portion of said tubular relief valve portion upstream of said chamber and configured to open if the pressure within said overpressure safety valve assembly adjacent said outlet portion end of said tubular body portion falls below a predetermined level, and a second relief valve mounted in said outlet portion of said tubular relief valve portion downstream of said chamber and configured to open if the pressure adjacent said outlet portion end of said overpressure safety valve assembly exceeds a predetermined level, and further wherein said tubular body portion and said tubular relief valve portion defines a flow channel for fluid flow from said outlet portion of said tubular body portion to said chamber.

* * * * *